United States Patent [19]

Stackman

[11] Patent Number: 4,683,327

[45] Date of Patent: Jul. 28, 1987

[54] ANISOTROPIC HEAT-CURABLE ACRYLIC TERMINATED MONOMERS

[75] Inventor: Robert W. Stackman, Racine, Wis.

[73] Assignee: Celanese Corporation, New York, N.Y.

[21] Appl. No.: 748,293

[22] Filed: Jun. 24, 1985

[51] Int. Cl.$^4$ .................... C07C 69/82; C07C 69/773
[52] U.S. Cl. .................................... 560/86; 526/325; 560/56; 560/59; 560/61; 560/62; 560/63; 560/64; 560/65; 560/67; 560/70; 560/80; 560/83; 560/85
[58] Field of Search ................ 560/80, 85, 86, 83, 560/56, 59, 64, 65, 67, 70, 61, 62, 63; 526/325

[56] References Cited

U.S. PATENT DOCUMENTS

| | | | |
|---|---|---|---|
| 3,336,360 | 8/1967 | Dill | 560/86 X |
| 3,770,811 | 11/1973 | Lee et al. | 560/221 |
| 4,068,082 | 1/1978 | Stoffey et al. | 560/90 |
| 4,144,283 | 3/1979 | Matsubasa | 560/221 X |
| 4,283,551 | 8/1981 | Chow et al. | 560/86 |
| 4,440,945 | 4/1984 | Conciatori et al. | 560/86 |
| 4,452,993 | 6/1984 | Conciatori et al. | 560/66 |

*Primary Examiner*—Natalie Trousof
*Assistant Examiner*—Vera C. Clarke
*Attorney, Agent, or Firm*—Burns, Doane, Swecker & Mathis

[57] ABSTRACT

A novel heat-curable acrylic-terminated monomer is provided which exhibits an optically anisotropic melt phase at a temperature which enables it to undergo melt processing in the formation of molded articles, etc. Subsequent to melt processing articles prepared from the monomer are capable of being cured to produce a thermoset self-reinforced composite which is soft and flexible relative to prior art monomers. The monomer may, for example, consist essentially of the reaction product of a methacrylic-substituted phenol and terephthalic acid.

17 Claims, No Drawings

ANISOTROPIC HEAT-CURABLE ACRYLIC TERMINATED MONOMERS

BACKGROUND OF THE INVENTION

The present invention is directed to anisotropic heat-curable monomers and to thermoset resins prepared therefrom.

Multi-functional heat-curable monomers are known which can be employed in the production of thermosetting composites such as, for example, epoxy-based compositions. However, one disadvantage with such known thermosetting compositions is that they tend to shrink to an undesirable degree subsequent to the crosslinking reaction.

It is also known to produce isotropic, heat-curable acrylic-terminated monomers. U.S. Pat. No. 4,452,993 to Conciatori et al (assigned to the assignee of the present invention) discloses such monomers having the formula:

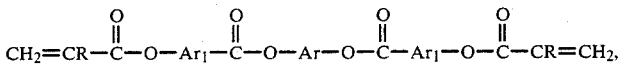

wherein $Ar_1$ is a divalent radical comprising at least one aromatic ring, $Ar_1$ is a divalent radical selected from the group consisting of phenylene, naphthalene, biphenylene and mixtures thereof and R is selected from the group consisting of hydrogen and methyl. Although the monomers of Conciatori et al possess the desirable characteristics of having self-reinforcing properties due to their ability to form a molecularly oriented anisotropic melt and of being crosslinkable due to their unsaturated end groups, due to the highly aromatic nature of the monomer (i.e., the monomer being devoid of aliphatic units in the main chain) the monomer is extremely rigid and quickly becomes brittle upon crosslinking. Further, the rigidity of the monomer may limit crosslinking of the same.

U.S. Pat. No. 3,770,811 to Lee et al discloses acrylic terminated compounds of the formula:

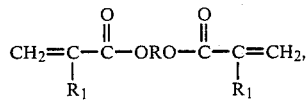

wherein R is selected from

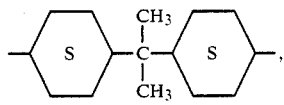

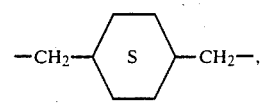

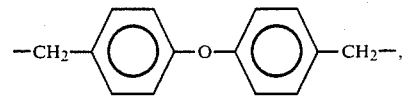

and

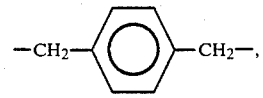

and $R_1$ is hydrogen, lower alkyl, or halogen, which compounds are said to be useful as binders in dental restorative compositions. However, these monomers, which contain one to two aromatic rings, are not capable of forming anisotropic melts and thus are not suitable for uses requiring a molecularly ordered polymer.

U.S. Pat. No. 3,066,112 to Bowen discloses a compound of the formula

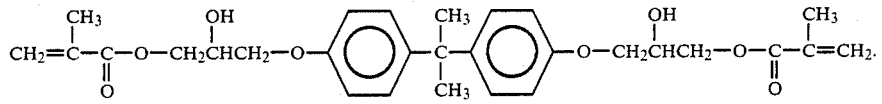

However, inasmuch as this compound has only two aromatic rings, it is likely to have the same defects as above.

Also, U.S. Pat. No. 3,657,384 to Yoshida et al discloses a thermoplastic copolymer prepared by copolymerizing at least one monoethylenically unsaturated carboxylic acid and an aminoplast with a monomer having the general formula

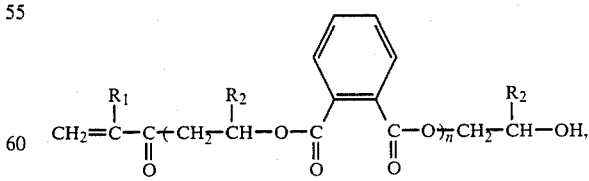

where n is an integer from zero to five. However, it is unlikely that either of the foregoing monomers form liquid crystalline melts due to the relatively high ratio of aliphatic to aromatic groups.

U.S. Pat. No. 2,928,804 to Foster et al discloses polymerizable esters of the general formula

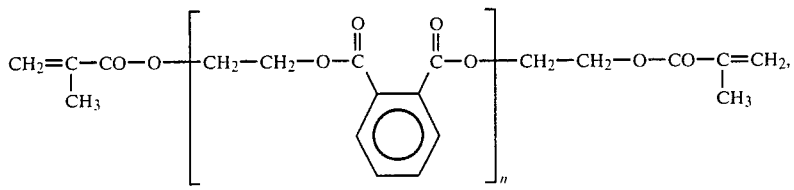

where n is an integer from zero to five. However, it is unlikely that either of the foregoing monomers form liquid crystalline melts due to the relatively high ratio of aliphatic to aromatic groups.

U.S. Pat. No. 4,068,082 to Stoffey et al discloses an ester of the following formula

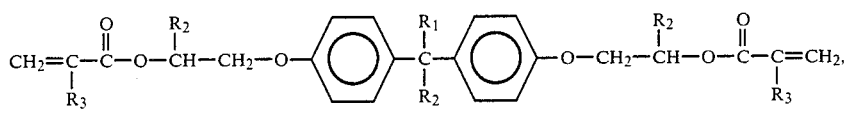

wherein $R_1$, $R_2$ and $R_3$ are either hydrogen or lower alkyl groups preferably comprising four or less carbon atoms. However, the same defects as above are likely to be present due to the low aromaticity of the monomer.

U.S. Pat. No. 4,144,283 to Matsubara discloses a curable coating composition of the formula:

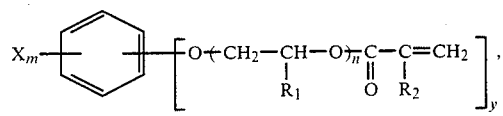

wherein X is selected from the group consisting of methyl and methoxy groups and a chlorine atom, $R_1$ and $R_2$ are each a hydrogen atom or methyl group, m is zero or one, y is an integer of two to four, and n is an integer of 1 to 10. However, these monomers do not form anisotropic melts.

OBJECTS OF THE INVENTION

It is therefore an object of the present invention to provide novel heat-curable monomers which exhibit reduced tendency to shrink upon curing.

It is also an object of the present invention to provide heat-curable monomers which permit a crosslinked resin to be formed therefrom which resin exhibits self-reinforcing characteristics due to molecular orientation in the resin.

It is a further object of the invention to provide heat-curable monomers which are flexible in the melt and which stay soft upon crosslinking relative to monomers known in the art, and which are capable of a higher degree of crosslinking than known monomers.

These and other objects as well as the scope, nature and utilization of the invention will be apparent from the following detailed description of the present invention and appended claims.

SUMMARY OF THE INVENTION

In accordance with the present invention, there is thus provided a novel heat-curable acrylic-terminated monomer capable of forming an anisotropic melt phase of the formula:

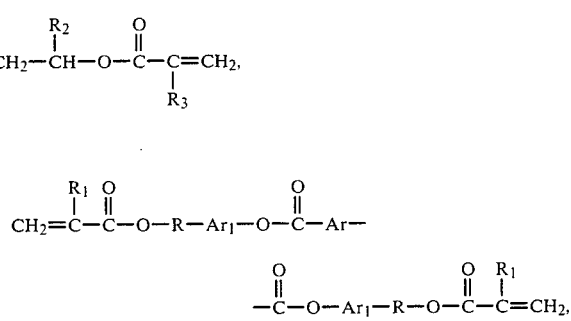

wherein Ar is a divalent radical comprising at least one aromatic ring, $Ar_1$ is a divalent radical selected from the group consisting of phenylene, naphthalene, biphenylene and mixtures thereof, R is selected from the group consisting of an alkylene group having from one to four carbon atoms and an oxyalkylene group having from one to four carbon atoms, and $R_1$ is selected from the group consisting of hydrogen and methyl, wherein hydrogen atoms present on the aromatic rings in the divalent radicals Ar and $Ar_1$ may be replaced by substitution selected from the group consisting of an alkyl group having one to four carbon atoms, an alkoxy group having one to four carbon atoms, halogen, phenyl, substituted phenyl, and mixtures thereof.

In accordance with another aspect of the present invention, there is provided a molded article formed from the above-described monomer which has been subjected to curing conditions for a time sufficient to accomplish substantial crosslinking.

DETAILED DESCRIPTION OF THE INVENTION

As stated above, the present invention relates to monomers of the formula

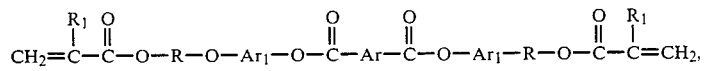

wherein Ar is a divalent radical comprising at least one aromatic ring, $Ar_1$ is a divalent radical selected from the group consisting of phenylene, naphthalene, biphenylene and mixtures thereof, R is selected from the group consisting of an alkylene group having from one to four carbon atoms and an alkoxy group having from one to four carbon atoms, and $R_1$ is selected from the group consisting of hydrogen and methyl, wherein hydrogen atoms present on the aromatic rings may be replaced by substitution selected from the group consisting of an alkyl group having one to four carbon atoms, an alkoxy group having one to four carbon atoms, halogen, phenyl, substituted phenyl, and mixtures thereof.

By way of example, the divalent radical Ar may include but is not limited to the following:

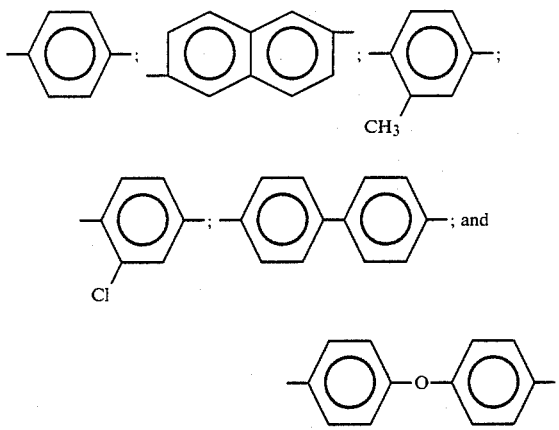

Again, the divalent radical $Ar_1$ may be phenylene, naphthalene, biphenylene, or mixtures thereof.

The preferred divalent radicals Ar and $Ar_1$ are each biphenylene.

At least some of the hydrogen atoms present upon one or more of the aromatic rings in the divalent radicals Ar and $Ar_1$ optionally may be replaced by a substituent selected from the group consisting of an alkyl group of one to four carbon atoms (e.g. methylene or ethylene), an alkoxy group of one to four carbon atoms (e.g., oxymethylene or oxyethylene), halogen (e.g., chlorine or bromine), phenyl, substituted phenyl (e.g., chlorophenyl) and mixtures thereof, provided such substitution does not ultimately prevent the monomer from forming an anisotropic melt phase. It is recognized, however, that such substitution may alter the temperature at which the phase transitions occur for the monomer (i.e., the transition from a solid to an anisotropic melt and from an anisotropic melt to a polymerized/crosslinked composition).

By way of example, R may be divalent alkylene radical consisting of from one to four carbon atoms, i.e., methylene, ethylene, propylene, or butylene, or a divalent oxyalkylene group consisting of from one to four carbon atoms, i.e., oxymethylene, oxyethylene, oxypropylene or oxybutylene, with the preferred R being ethylene or oxyethylene. $R_1$ is selected from the group consisting of hydrogen and methyl, with methyl being preferred.

It has been surprisingly and unexpectedly discovered that the heat-curable monomers of the present invention can be employed with significant advantage in the production of thermosetting polyester resins. Such resins would be expected to exhibit shrinkage subsequent to being cured due to the fact that such monomers are capable of forming an anisotropic melt phase upon being heated to the melting temperature of the monomer, and would be expected to be extremely rigid, forming a brittle resin when crosslinked.

Unlike monomers commonly encountered in the prior art, the monomers of the present invention are capable of forming an anisotropic melt phase whereby an atypical degree of order is manifest in the molten monomer. The monomer readily forms liquid crystals in the melt phase and accordingly exhibits a high tendency for the monomer chains to orient in the shear direction, with such anisotropic properties being exhibited at temperatures which are amenable to melt processing to form shaped articles. Such order in the melt may be confirmed by conventional polarized light techniques whereby crossed polarizers are utilized. The anisotropic melt phase may be confirmed by the use of a Leitz polarizing microscope at a magnification of 40X with the sample on a Leitz hot stage and under nitrogen atmosphere. The monomer melt is optically anisotropic, i.e., it transmits light when examined between crossed polarizers. The amount of light transmitted increases when the sample is optically anisotropic even in the static state.

It has also been surprisingly and unexpectedly found that the polymers prepared from the monomers of the present invention, prior to crosslinking, are far more flexible than polymers prepared from monomers having no aliphatic units in the main chain. This flexibility allows the polymer which results to crosslink more completely than polymers from known monomers, and produces a polymer which, upon crosslinking, is far less brittle than prior art monomers.

More specifically, the monomers of the present invention may include but are not limited to terephthaloyl-bismethacryloyloxymethylenephenolate, terephthaloyl-bismethacryloyloxyethylenephenolate, terephthaloyl-bis-acryloylmethylenephenolate, terephthaloyl-bis-acryloylmethylenephenolate, terephthaloyl-bis-acryloylmethylenephenolate, terephthaloyl-bisacryloylethylenephenolate, terephthaloyl-bis-oxymethylenephenolate, and terephthaloyl-bis-acryloyloxyethylenephenolate. The preferred monomers are terephthaloyl-bis-methacryloyloxyethylenephenolate, i.e.,

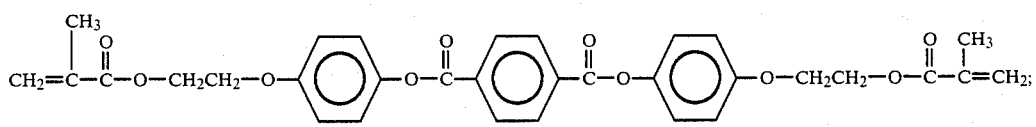

terephthaloyl-bis-methacryloylethylenephenolate, i.e.,

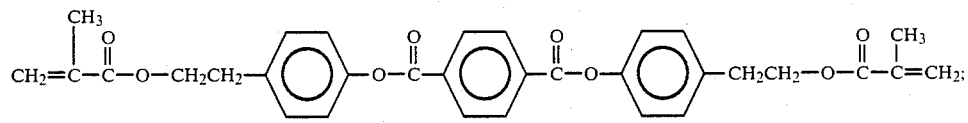

terephthaloyl-bis-acryloyloxyethylenephenolate, i.e.,

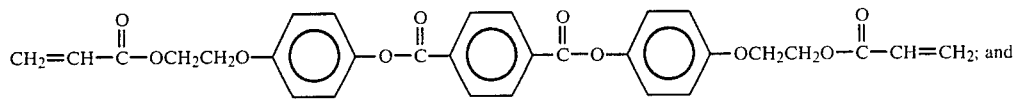

terephthaloyl-bis-acryloylethylenephenolate, i.e.,

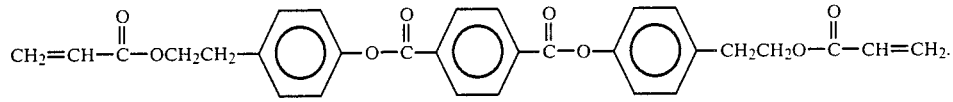

The most preferred monomers are terephthaloyl-bis-methacryloyloxyethylenephenolate and terephthaloyl-bis-methacryloylethylenephenolate.

As noted previously, the monomers of the present invention are capable of forming an anisotropic melt phase upon being heated to the necessary phase transition temperature. The monomers will retain such anisotropic characteristics upon being heated to increasingly higher temperatures whereupon the monomer will begin to polymerize and/or crosslink at a temperature in excess of the melting temperature of the monomer and form a thermosetting polymeric resin. The resin advantageously retains the high degree of orientation exhibited by the monomer molecules prior to such polymerization, with the orientation of the molecules in the resin providing a self-reinforcing effect.

The monomers of the present invention may be formed by a variety of ester forming techniques. In a preferred embodiment, the monomer is prepared by an ester-forming technique whereby an acrylic-terminated phenol (e.g., p-methacryloyloxyethylenephenol) and a difunctional aromatic moiety (e.g., terephthalic acid) possessing the required aromatic and alkyl groups and possessing carboxyl and hydroxyl groups are reacted which, upon condensation, form the requisite monomer. The phenol and difunctional aromatic moiety are reacted in a molar ratio ranging from about 2:0.5 to about 2:1. The organic monomer compounds may be reacted in the absence of a heat exchange fluid via a melt acidolysis procedure. They, accordingly, may be heated initially from a melt solution of the reactants with the reaction continuing as polymer particles are suspended therein. A vacuum may be applied to facilitate removal of volatiles formed during the condensation.

The monomers of the present invention can be molded or otherwise melt processed and then cured to yield a polymerized composite of high strength due to the self-reinforcing characteristics of the oriented molecules. Such melt processing may be performed at a temperature significantly (i.e., at least 20° C.) below the crosslinking (curing) temperature of the monomer to prevent premature crosslinking. The composite will also exhibit desirable thermal and chemical stability. The monomers can be melt processed to form a variety of shaped articles by conventional extrusion and injection molding techniques.

Such molding compositions may optionally include various types of fillers (e.g., talc) in amounts of about 1 to 60 percent by weight as well as various types of reinforcing agents (e.g., glass fibers) in amounts of about 1 to 60 percent by weight.

Subsequent to molding, the article is treated under curing conditions for a time sufficient to accomplish substantial crosslinking. Curing may be accomplished either thermally or radiationally, e.g., by subjecting to an electron beamer or to ultraviolet irradiation according to techniques known in the art. When thermal crosslinking is performed, it is beneficial to raise the temperature gradually to prevent melting of the shaped article.

The monomers of the present invention may also be employed as protective coatings on various substrates in the form of the crosslinked resin. The monomers can also be employed as the matrix material for a web of infusible fibers such as glass fibers wherein the monomer is applied to the web in an anisotropic melt state and subsequently heat-cured. Such methods are well known in the art and will not be discussed in greater detail herein.

The invention is additionally illustrated in connection with the following Examples which are to be considered as illustrative of the present invention. It should be understood, however, that the invention is not limited to the specific details of the Examples.

EXAMPLE I

To a three-necked, one-liter flask containing 100 milliliters of ether and equipped with a condenser and stirrer under argon is added 33.3 g (0.276 moles) of methacryloylchloride and an equal volume of methylene chloride. To the solution is then added 42.5 g (0.276 moles) of 4-(2-hydroxyethoxy)phenol, 300 ml of methylene chloride, and 27.9 g (0.276 moles) of triethylamine (added dropwise) with stirring, and this mixture is allowed to cool. The mixture is allowed to stand overnight, after which time it is separated, washed and recrystallized from aqueous ethanol to yield p-methacryloyloxyethylenephenol.

The p-methacryloyloxyethylenephenol product is placed in a three-necked flask equipped with a nitrogen inlet and outlet, mechanical stirrer and distillation head. 129.7 g of terephthaloyl chloride and (0.552 moles) methylene chloride (as a solvent) is added. Triethylamine as an acid acceptor (25 milliliters) is also added slowly and the mixture is stirred for 16 hours. The methylene chloride is then evaporated on a rotary evaporator. The residue is washed with water and 5 percent sodium bicarbonate, rewashed with water and dried in air to yield terephthaloyl-bis-methacryloyloxyethylenephenolate.

EXAMPLE II

The process of Example I is substantially followed except that, in lieu of 4-(2-hydroxyethoxy)phenol, is added 38.1 g (0.276 moles) of 4-(2-hydroxyethyl)-phenol, to yield terephthaloyl-bis-methacryloylethylenephenolate.

The principles, preferred embodiments and modes of operation of the present invention have been described in the foregoing specification. The invention which is intended to be protected herein, however, is not to be construed as limited to the particular forms disclosed, since these are to be regarded as illustrative rather than restrictive. Variations and changes may be made by those skilled in the art without departing from the spirit of the invention.

I claim:

1. Heat-curable acrylic-terminated monomer capable of forming an anisotropic melt phase of the formula:

$$CH_2=C(R_1)-C(=O)-O-R-Ar_1-O-C(=O)-Ar-$$
$$-C(=O)-O-Ar_1-R-O-C(=O)-C(R_1)=CH_2,$$

wherein Ar is a divalent radical comprising at least one aromatic ring, $Ar_1$ is a divalent radical selected from the group consisting of phenylene, naphthalene, biphenylene and mixtures thereof, R is selected from the group consisting of an alkylene group having from one to four carbon atoms and an oxyalkylene group having from one to four carbon atoms, and $R_1$ is selected from the group consisting of hydrogen and methyl, wherein hydrogen atoms present on the aromatic rings in said divalent radicals Ar and $Ar_1$ may be replaced by substitution selected from the group consisting of an alkyl group having one to four carbon atoms, an alkoxy group having one to four carbon atoms, halogen, phenyl, and mixtures thereof.

2. A heat-curable monomer according to claim 1 wherein Ar is selected from the group consisting of

[phenylene; naphthalene; methylphenylene;

chlorophenylene; biphenylene; and diphenyl ether]

3. A heat-curable monomer according to claim 1 wherein Ar is

[phenylene]

4. A heat-curable monomer according to claim 1 wherein Ar is

[methylphenylene]

5. A heat-curable monomer according to claim 1 wherein Ar is

[chlorophenylene]

6. A heat-curable monomer according to claim 1 wherein Ar is

[diphenyl ether]

7. A heat-curable monomer according to claim 1 wherein Ar is

[biphenylene]

8. A heat-curable monomer according to claim 1 wherein Ar is

[naphthalene]

9. A heat-curable monomer according to claim 1 wherein $Ar_1$ is

[phenylene]

10. A heat-curable monomer according to claim 1 wherein R is ethylene.
11. A heat-curable monomer according to claim 1 wherein R is oxyethylene.
12. A heat-curable monomer according to claim 1 wherein $R_1$ is hydrogen.
13. A heat-curable monomer according to claim 1 wherein $R_1$ is methyl.
14. Terephthaloyl-bis-methacryloyloxyethylenephenolate.
15. Terephthaloyl-bis-methacryloylethylenephenolate.
16. Terephthaloyl-bis-acryloyloxyethylenephenolate.
17. Terephthaloyl-bis-acryloylethylenephenolate.

* * * * *